US00PP23601P3

(12) United States Plant Patent
Olesen

(10) Patent No.: US PP23,601 P3
(45) Date of Patent: May 21, 2013

(54) CLIMBING ROSE PLANT NAMED 'POULCY017'

(50) Latin Name: ***Rosa* hybrid**
Varietal Denomination: Poulcy017

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 8 days.

(21) Appl. No.: 13/317,265

(22) Filed: Oct. 13, 2011

(65) Prior Publication Data

US 2013/0097741 P1 Apr. 18, 2013

(51) Int. Cl.
*A01H 5/00* (2006.01)

(52) U.S. Cl.
USPC ..... Plt./111; Plt./109

(58) Field of Classification Search
USPC ..... Plt./109, 111
See application file for complete search history.

*Primary Examiner* — Susan McCormick Ewoldt

(57) ABSTRACT

A new garden rose plant of the climbing rose class which has abundant, yellow flowers and attractive foliage. This new and distinct variety has shown to be uniform and stable in the resulting generations from asexual propagation.

3 Drawing Sheets

Botanical designation: *Rosa* hybrid.
Variety denomination: 'Poulcy017'.

SUMMARY OF THE INVENTION

The present invention constitutes a new and distinct variety of garden rose plant which originated from a controlled crossing between the female seed parent, an unnamed seedling, and the male pollen parent, an unnamed seedling.

The two parents were crossed during the summer of 2002 and the resulting seeds were planted in a controlled environment in Fredensborg, Denmark. The new variety, named 'Poulcy017', originated as a single seedling from the stated cross.

The new variety may be distinguished from its female seed parent primarily by flower color. The seed parent has pink flowers while the new variety has yellow flowers.

The new variety may be distinguished from its male pollen parent primarily by growth habit. The male pollen parent is bushy and upright while the new variety is arching.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots;
3. Exceptional disease resistance.
4. Reduced apical dominance in flowering habit. The new variety consistently produces flowers evenly from the lower branches to the top of the plant.

This combination of qualities is not present in previously available commercial cultivars of this type, known to the inventor, and distinguish 'Poulcy017' from all other varieties of which we are aware.

As part of the rose development program, Mogens N. Olesen germinated the seeds from the aforementioned hybridization during winter of 2002 and conducted evaluations on the resulting seedlings in a controlled environment in Fredensborg, Denmark. 'Poulcy017' was selected in the spring of 2003 by the inventor as a single plant from the progeny of the aforementioned hybridization.

Asexual reproduction of 'Poulcy017' by traditional budding and rooted cuttings was first done by Mogens N. Olesen in the nursery in Fredensborg, Denmark in July, 2003. This initial and other subsequent asexual propagations conducted in controlled environments have demonstrated that the characteristics of 'Poulcy017' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulcy017'. Specifically illustrated in the drawing are.

DETAILED DESCRIPTION OF THE VARIETY

Figure 1:
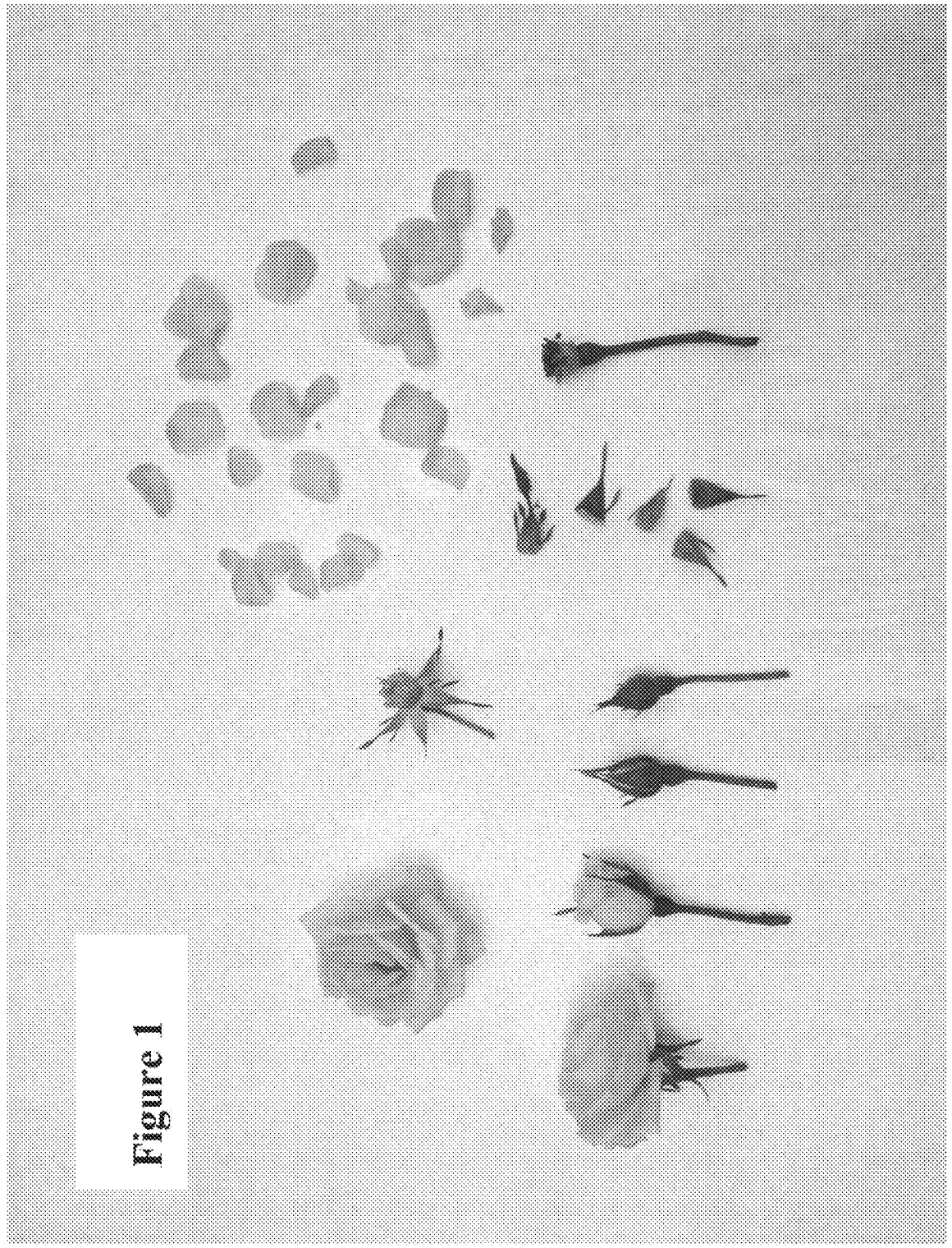
FIG. 1; Flowers at various stages of opening, petals and sepals detached.
Figure 2:
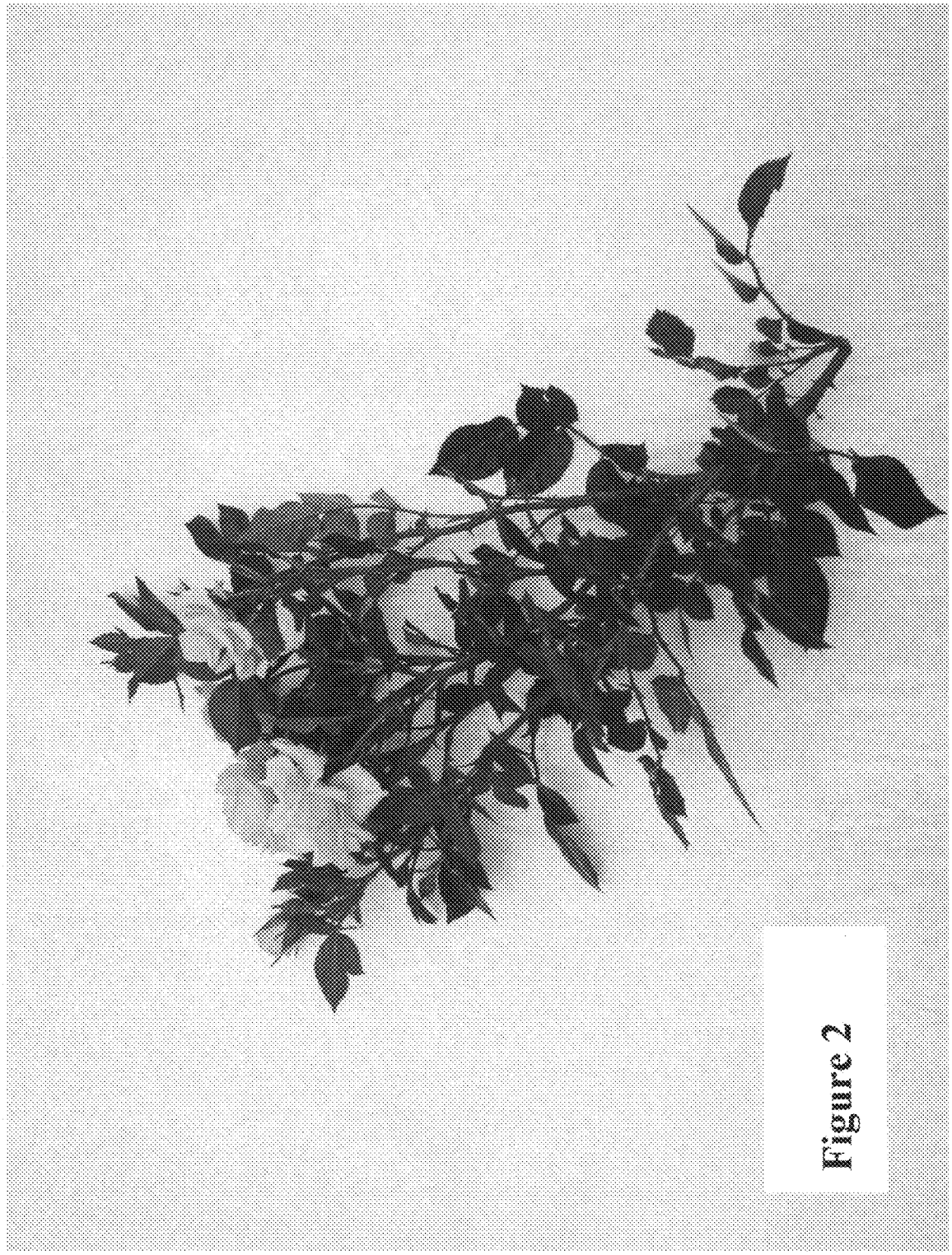
FIG. 2; Cluster of flowers on branch showing attachment of flower buds and leaves.
Figure 3:
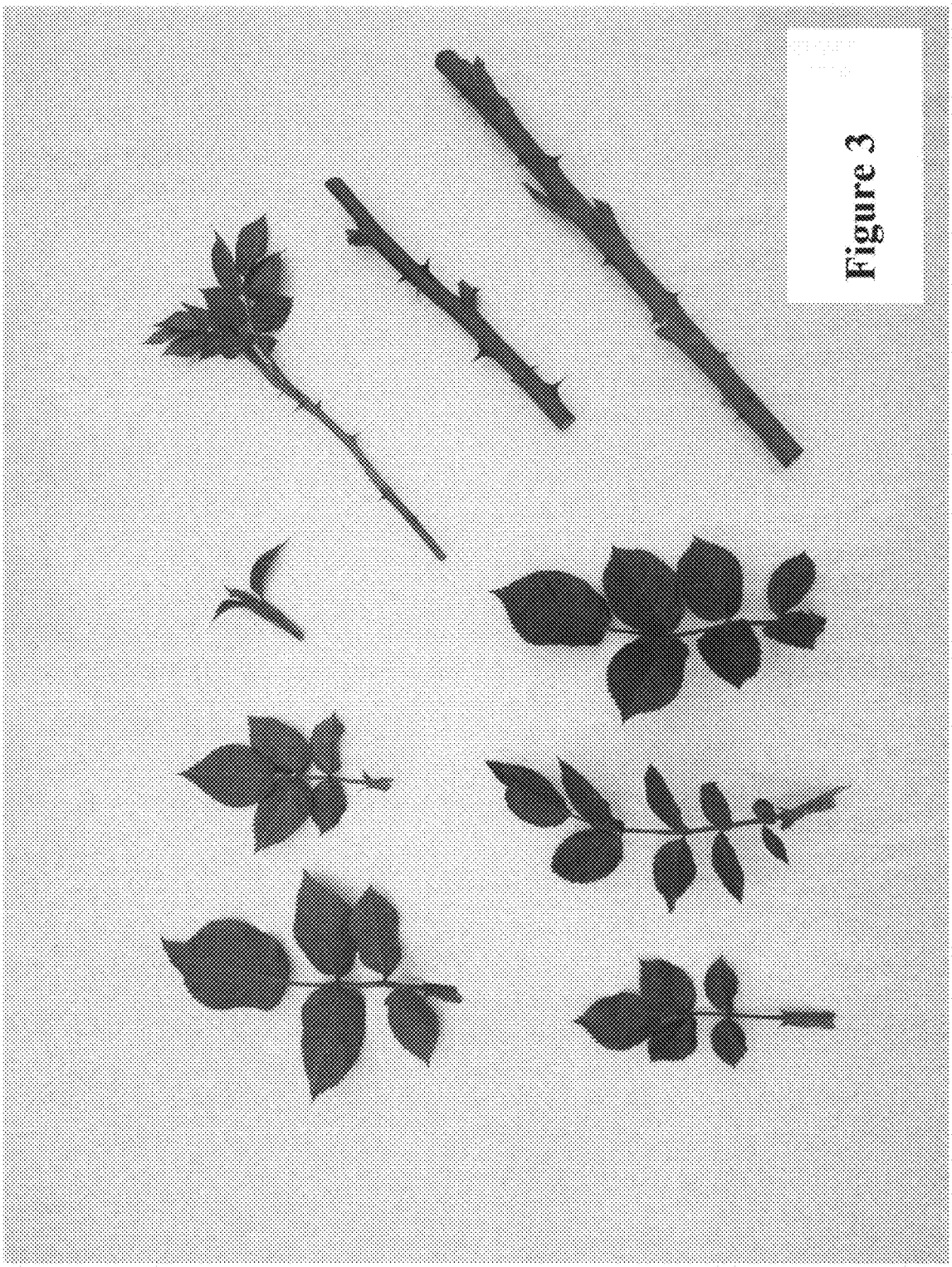
FIG. 3; Leaves and stems.

The following is a description of 'Poulcy017', as observed in its growth in a field nursery in Benton County Oreg. Observed plants are 20 months of age, grown from own root. Color references are made using The Royal Horticultural Society (London, England) Colour Chart, 2001, except where common terms of color are used.

For a comparison, several physical characteristics of the rose variety 'Poulyc004', U.S. Plant Pat. No. 15,502 are compared to 'Poulcy017' in Chart 1.

CHART 1

| | 'Poulcy017' | 'Poulyc004' |
|---|---|---|
| Normal number of leaflets leaves in middle of the stem | 7 | 5 |

CHART 1-continued

| | 'Poulcy017' | 'Poulyc004' |
|---|---|---|
| Flower Diameter | 40-45 mm | 30-35 mm |
| After opening, upper surface of flower petals | Yellow Group 10A | Yellow Group 13A |

FLOWER AND FLOWER BUD

Blooming habit: Early flowering, in stages of continuous periods of bloom.

Flower bud:

*Size*.—Upon opening, 30 mm in length from base of receptacle to end of bud. Bud diameter is 10 mm.

*Bud form*.—Ovoid.

*Bud color*.—As sepals unfold, petals are Yellow Group 11A.

*Sepal inner surface*.—Color: Yellow-Green Group 146C with weak anthocyanic pigments Greyed-Red Group 182A. Surface: Smooth, weak pubescence observed.

*Sepal outer surface*.—Color: Yellow-Green Group 144A. Weak anthocyanic pigments Greyed-Red Group 182A. Texture: Smooth.

*Sepal shape*.—Apex: Cirrhose. Base: Flat at union with receptacle.

*Sepal margin*.—Margins have medium foliaceous appendages on three of the five sepals.

*Sepal size*.—30 mm long by 10 mm wide.

*Receptacle*.—Texture: Smooth. Shape: Elliptical. Size: 7 mm tall by 5 mm wide. Color: Yellow-Green Group 144A. Weak anthocyanic pigments the color of Greyed-Red Group 178A.

*Pedicel*.—Surface: Smooth. Length: 30 mm on average. Diameter: 2 mm on average. Color: Yellow-Green Group 144A. Anthocyanic pigments the color of Greyed-Red Group 181A observed. Strength: Moderate.

Peduncle:

*Size*.—60 to 70 cm in length by 2.5 mm wide on average.

*Color*.—Yellow-Green Group 144A.

*Texture*.—Smooth.

Flower bud development: Flower buds are borne in clusters of 7 to 21 flower buds per flowering branch resembling a corymb. Reduced apical dominance in flower habit causes flower buds develop in stages evenly from the base of the plant to the upper branches.

Flower bloom:

*Fragrance*.—Light spicy fragrance.

*Duration*.—The blooms have a duration on the plant of approximately 10 days. Petals fall cleanly away from plant after flowers have fully matured.

*Size*.—Flower diameter is 40 to 45 mm when open. Flower depth is 20 mm.

*Flower shape*.—General shape is an open cup with petals that curve out from the center.

*Shape of flower, side view*.—Upon opening the upper portion is flat. The lower portion is a flattened convex.

Petalage: Under normal conditions, flowers have 27 petals total, 3 to 5 of which are petaloids.

Petal color:

*Upon opening, outer petals*.—Upper surface: Yellow Group 10A with faint intonations of Yellow Group 13B. Lower surface: Yellow Group 10A.

*Upon opening, inner petals*.—Upper surface: Yellow Group 12A with intonations of Yellow Group 13B. Lower surface: Yellow Group 13B.

*Basal petal spots*.—Upon opening, no distinctive coloration at the petal base observed.

*After opening, outer petals and inner petals*.—Upper surface: Yellow Group 10A. Lower surface: Yellow Group 10B.

*Basal petal spots*.—After opening, no distinctive coloration at the petal base observed.

General tonality: On open flower Yellow Group 10A. After 7 days, the general tonality is Yellow Group 8B.

Petals:

*Petal reflex*.—Medium to strong.

*Margin*.—Entire and uniform. Occasionally a weak point at the center of the margin.

*Shape*.—Generally narrow elliptic to ovate. Apex shape: Round. Base shape: Acute.

*Size*.—25 mm (l)×10 to 20 mm (w).

*Texture*.—Smooth.

*Thickness*.—Average.

Petaloids:

*Quantity*.—3 to 5.

*Shape*.—Irregular, asymmetric, and obovate. The base is acute. Apex is rounded.

*Color*.—Upper surface is Yellow Group 10A. Lower surface is Yellow Group 10B.

*Size*.—15 mm long by 11 mm wide.

Reproductive organs:

*Pollen*.—None observed.

*Anthers*.—Size: 2 mm in length. Color: Yellow-Orange Group 17C. Quantity: On average 95.

*Filaments*.—Color: Yellow Group 13A. Length: 6 mm.

*Pistils*.—Length: 3 mm. Quantity: 60 on average.

*Stigmas*.—Inferior in location relative to the length of the filaments and the height of the anthers. Color: Yellow-Green Group 145C.

*Styles*.—Color: Yellow-Green Group 145C.

*Hips*.—None Observed.

PLANT

Plant growth: Arching. As an own root plant the average height of the plant is 80 cm and the average width is 60 cm.

Stems:

*Color*.—Juvenile growth: Yellow-Green Group 144A with anthocyanic intonations of Greyed-Red Group 178A. Mature growth: Yellow-Green Group 144A.

*Length*.—Canes are 25 to 55 cm from the base of the plant to the flowering portion.

*Diameter*.—8 mm.

*Internodes*.—On mature canes, 15 to 30 mm between nodes.

*Surface texture*.—Young wood: Smooth. Older wood: Smooth.

Long prickles:

*Incidence*.—6 prickles per 10 cm of stem.

*Size*.—Average length of prickles on mature stems is 4 mm.

*Shape*.—Concave.

*Color*.—Juvenile prickles: Greyed-Purple Group 185A. Mature prickles: Greyed-Red Group 180B.

Plant foliage: Normal number of leaflets leaves in middle of the stem is 7. Occasionally there are 9 leaflets.

*Compound leaf*.—110 to 120 mm (l)×65 (w).

*Quantity*.—3 to 4 leaves per 10 cm of stem.

*Color of mature foliage*.—Upper side: Yellow-Green Group 147A. Lower side: Yellow-Green Group 144B.

*Color of juvenile foliage*.—Upper side: Yellow-Green Group 144A. Lower side: Yellow-Green Group 144B. Anthocyanin: Greyed-Red Group 178A located on the leaflet margins.

Plant leaves and leaflets:

*Stipules*.—Size: 18 to 20 mm in length. Quantity: 2 per compound leaf. Shape: Linear, slightly broad based with outward extending apices. Margins: Finely serrated with few stipitate glands. Color: Yellow-Green Group 144A.

*Petiole*.—Length: 18 to 25 mm. Diameter: 2 mm.

*Upper surface*.—Color: Greyed-Red Group 181C.

*Lower surface*.—Color: Yellow-Green Group 144A. Observations: Small prickles observed.

*Rachis*.—Length: 50 to 70 mm.

*Upper surface*.—Color: Greyed-Red Group 181C.

*Lower surface*.—Color: Yellow-Green Group 144A. Observations: Small prickles observed. Margin: Serrate. Size: Average size of the terminal leaflet on normal leaves is 40 mm in length by 25 mm wide. Shape: Generally elliptical. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery and downy mildew, rust, black spot, and Botrytis under normal growing conditions in Benton County Oreg.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the climbing rose class named 'Poulcy017', substantially as illustrated and described herein, due to its abundant yellow flowers, disease resistance, and extended period of bloom.

* * * * *